United States Patent
Clifton et al.

(10) Patent No.: US 8,718,989 B2
(45) Date of Patent: May 6, 2014

(54) METHOD TO DETERMINE THE INTERNAL STRUCTURE OF A HEAT CONDUCTING BODY

(75) Inventors: Andrew Clifton, Davos (CH); Martin Schnieder, Ennetbaden (CH); Chiara Zambetti, Baden (CH)

(73) Assignee: Alstom Technology Ltd., Baden (CH)

( * ) Notice: Subject to any disclaimer, the term of this patent is extended or adjusted under 35 U.S.C. 154(b) by 1766 days.

(21) Appl. No.: 11/429,954

(22) Filed: May 9, 2006

(65) Prior Publication Data

US 2006/0256837 A1 Nov. 16, 2006

Related U.S. Application Data

(63) Continuation of application No. PCT/EP2004/052955, filed on Nov. 15, 2004.

(30) Foreign Application Priority Data

Dec. 1, 2003 (EP) ..................................... 03104466

(51) Int. Cl.
*G06F 17/50* (2006.01)

(52) U.S. Cl.
USPC .......................................................... 703/5

(58) Field of Classification Search
USPC .......................................................... 703/5
See application file for complete search history.

(56) References Cited

U.S. PATENT DOCUMENTS

| | | |
|---|---|---|
| 3,566,669 A | 3/1971 | Lawrence et al. |
| 6,142,662 A * | 11/2000 | Narh et al. ....................... 374/44 |
| 6,422,743 B1 | 7/2002 | Nirmalan et al. |
| 2003/0055594 A1 * | 3/2003 | Bunker et al. ................. 702/134 |
| 2003/0128737 A1 * | 7/2003 | McGrath et al. ............... 374/161 |
| 2003/0171889 A1 * | 9/2003 | Shelby et al. .................. 702/130 |

OTHER PUBLICATIONS

Mackley et al. "Heat Transfer and Associated Energy Dissipation for Oscillatory Flow in Baffled Tubes". Chemical Engineering Science, vol. 50, No. 14, pp. 2211-2224, 1995.*
Ekkad et al. "A Transient Liquid Crystal Thermography Technique for Gas Turbine Heat Transfer Measurements", 2000 Meas. Sci. Technology.*
By: Nirm V. Nirmalan et al. "The measurement of full-surface internal heat transfer coefficients for turbine airfoils using a non-destructive thermal inertia technique", Journal of Turbomachinery vol. 125, p. 83, Jan. 2003.
European Search Report.

* cited by examiner

*Primary Examiner* — Shambhavi Patel
(74) *Attorney, Agent, or Firm* — Buchanan Ingersoll & Rooney PC

(57) ABSTRACT

In a non-destructive method for determining the internal structure of a heat conducting body, such as a cooling structure of a turbine blade, a flow medium is passed through the internal structure and the resultant thermal image on an external surface of the body is registered using a pixelised thermal image detector. Heat transfer coefficients and wall thicknesses of the internal structure are determined by means of a 1-,2-, or 3-dimensional inverse method that includes the numerical modelling of the surface temperatures using initial values for heat transfer coefficients and wall thicknesses and an optimization of the values using an iteration method. In a special variant of the method, the spatial geometry of the internal structure of the body is determined by means of the same inverse method and a geometry model that is optimised by iteration. No prior knowledge of the internal geometry is required.

8 Claims, 2 Drawing Sheets

METHOD TO DETERMINE THE INTERNAL STRUCTURE OF A HEAT CONDUCTING BODY

TECHNICAL FIELD

The invention pertains to a non-destructive method to determine the heat transfer characteristics of a heat conducting body having an internal structure using a heat transfer measurement by means of infrared surface imaging.

BACKGROUND ART

The internal structure of turbine blades, internal combustion engines, electrical motors, household or industrial heaters or any heat conducting body having a internal flow circuit may be determined non-destructively and non-intrusively by means of heat transfer measurements. Such measurements allow inspection and quality control of the internal geometry and heat transfer parameters of the body where direct measurement is not possible.

In methods of the state of the art, measured temperature data of a body to be inspected is compared to data available from a body serving as a standard with known geometry and heat transfer characteristics. In further methods, the determination of heat transfer coefficients of the body to be inspected requires prior knowledge of the internal geometry and material properties.

In U.S. Pat. No. 3,566,669 to Lawrence a heating of cooling fluid is passed through a body, such as a turbine blade, whose internal structure is to be determined. A temperature pattern resulting on its external surface is measured and compared to the pattern of a standard body of known wall thicknesses and subjected to the same fluid flow. An obstruction in a cooling passage may be determined by comparison of adjacent exterior areas of the body.

U.S. Pat. No. 6,422,743 to Nirmalan discloses a non-destructive method for quantitatively determining heat transfer characteristics of a cooled structure. The method includes an infrared thermal imaging of the surface of a body that has been heated and through which a cooling medium is passed. Transient surface temperature data is acquired in pixel format using an infrared thermal imaging device and converted into a format including time, two-dimensional geometric position, and temperature. Heat transfer coefficients are obtained for each pixel on the surface of the body and for each time increment by processing the data using a numerical solution of a transient heat balance equation and taking a time average of the coefficient.

While this method allows the determination of heat transfer coefficients, it does not provide means to determine internal geometrical parameters of the body. An evaluation of the quality of a body is assessed by a comparison to a known body of its kind.

In the article by Nirm V. Nirmalan et al., "The measurement of full-surface internal heat transfer coefficients for turbine airfoils using a non-destructive thermal inertia technique", Journal of Turbomachinery, Vol. 125, p. 83, January 2003, discloses a further method for determining heat transfer coefficients by means of thermal surface imaging. A body having internal flow structure is transiently heated or cooled by a heating or cooling medium of known temperature and flow rate. A two-dimensional pixelised infrared camera records the external surface temperature as a function of time. This transient thermal history contains the response data according to the internal heat transfer coefficients.

The internal heat transfer coefficient distribution is obtained by an iterative method that predicts the external surface temperatures using a finite element model of finite volume model and compares them to the measured temperatures. In case of insufficient fit to the measured values, the heat transfer coefficient is recalculated using an updated model. In the calculation of the heat transfer coefficients it is assumed that the walls of the internal structure conduct heat in one dimension only and heat conduction in lateral directions are negligible. Furthermore, the prediction of the external surface temperature requires known values of the body's internal wall thicknesses and structure geometry, material properties, and temperatures of the transient fluid. The method is therefore limited to bodies, for which these values are already known or which are determined by other methods.

The described methods are limited to the measurement of bodies for which the geometry of the internal structure is known or that is determined by another non-destructive method.

SUMMARY OF THE INVENTION

It is an object of the invention to provide a non-destructive method to determine the heat transfer characteristics of a heat conducting body having an internal structure for a flow circuit. It is a particular object of the invention to provide such method for determining the heat transfer coefficients of the body together with the wall thicknesses of the internal structure in the same analysis process and without prior knowledge of the body's internal geometry. The method is to use thermal images that result on an external surface of the body from a transient flow passed through the body's internal structure.

The method comprises the following steps:

Passing a flow medium through a body having an internal structure for a flow circuit for a flow medium, registering a thermal image of an external surface of the body as a function of time using a pixelised image detector, processing the pixelised thermal image in order to obtain measured surface temperatures for a given set of points in time and a given set of points on the external surface of the body, predicting temperatures on same external surface resulting from the flow medium through the body using a numerical model, comparing the measured surface temperatures to the predicted surface temperatures, iterating the prediction of the surface temperatures in order to optimise a fit between the temperature data measured by the thermal image detector and the temperature data predicted by the numerical model.

According to the invention, the numerical model includes initial values for the heat transfer coefficients and the wall thicknesses of the internal structure. These initial values are based on a good estimate and not on a prior knowledge of the body's internal structure. A best fit method is applied to the predicted and measured surface temperature values. In case of an insufficient fit, the values for heat transfer coefficients and wall thicknesses are optimised in an iteration of the method in order to optimise the fit between the measured and predicted surface temperatures. The iteration is repeated until an optimal fit is obtained, in which case the heat transfer coefficients together with the wall thicknesses of the internal structure are determined. In particular, the numerical method does not include known parameters of the geometry of the internal structure or the structure's materials.

In a preferred variant of the method according to the invention, the iteration of the prediction of the surface temperatures includes a two- or three-dimensional model of the geometry of the body's internal structure. The spatial parameters of the geometry model are optimised at each iteration. In the event of an optimal fit between predicted and measured surface temperatures, the body's geometry together with the heat transfer characteristics are determined using the one single method. Thus, along with the heat transfer characteristics the location, size, and shape of the internal passages of the cooling structure may be determined.

The method analyses the thermal surface response and uses an inverse 1-, 2-, or 3-dimensional method to determine the heat transfer characteristics together with wall thicknesses that correspond to the thermal response.

Optionally, it allows also the determination of the above mentioned parameters in combination with the internal heat flux of the transient flow medium passing through the structure as well as the structure geometry.

The measured (and predicted) surface temperatures are analysed by considering the temperature data from an array of pixels of the image detecting device at one time. (rather than only one pixel with consideration of the effect of four immediately adjacent pixels, as is done in the method according to U.S. Pat. No. 6,422,743).

The method according to the invention allows the consideration of a spatial and temporal temperature gradient through an internal wall of the body, i.e. it considers walls having thicknesses such that there is a temperature gradient across them. This allows for more accurate and unambiguous determination of heat transfer coefficients and wall thicknesses. (An assumption of relatively thin walls of a zero temperature gradient across them may lead on the other hand to ambiguous and inaccurate results.

The method also considers temperature gradients not only normal to a wall of the internal structure, but also in lateral directions, i.e. in two or three dimensions. This allows the consideration of the effects of heat transfer in wall structures of high curvatures as is often found in serpentine structures.

The method according to the invention allows the inspection of existing bodies, such as gas turbine blades having a complex internal cooling structure, for which the internal geometry is not known. The method allows the distinction and analysis of cooling structure features such as impingement ribs, pin fins, bends, and even blade showerheads. In particular, it takes into account and allows the determination of features having a small radius of curvature, which is often the case in serpentine type cooling structures of turbine blades.

The method may be applied in the qualification of geometry and heat transfer characteristics as part of the design and manufacturing process of turbine blades. Furthermore, it may be used for the determination of the potential lifetime of such blades and for the inspection of existing blades, for which internal geometry data is not available.

The method according to the invention provides a time and cost efficient inspection of a given body. Heat transfer characteristics as well as geometric parameters may be determined without the need of any additional measurements or of an additional measurement device such as ultra-sound.

In a preferred method according to the invention, the quality of the fit between the predicted and measured temperature values of the surface temperature is determined by analysis of one or more of the following criteria:
The absolute temperature at a given pixel,
the change of temperature from the initial temperature over time,
local derivative of temperature with respect to time or space, or a combined local derivative according to the above.

The iteration of the numerical model includes a minima-seeking routine applied to the difference between the values of the predicted and measured temperature values.

In a further preferred method according to the invention, one or more of the following characteristics is applied to the parameters included in the numerical model:
the wall thicknesses are finite and have a zero temperature gradient across it,
the wall thicknesses are finite and the walls have a finite temperature gradient across them normal to the wall,
the wall thicknesses are finite and the walls have a finite temperature gradient in two or three dimensions.

In a further preferred method, a finite element or boundary model of the internal structure of the body is applied.

In a variant of this method, the model of the body's geometry is modified as necessary, in order to determine the body's geometry. Along with this modification the heat transfer coefficients, wall thicknesses and local heat flux may also be modified.

In a further variant of the method according to the invention, a first flow medium is passed through the body and a first set of surface temperatures is taken as a function of time and space. A second flow medium, having a temperature different from the first flow medium, is passed through the internal structure of the body at the same pressure conditions as for the first flow medium. A second set of surface temperatures of same external surface of the body is taken that is different from the first temperature data set using the same pixelised thermal image detector as for the first set of data. The inverse method as described above and in claim 1 for determining the heat transfer characteristics and the geometry of the internal structure of the body is performed on both sets of temperature data including the iteration and minimisation of the fit between predicted and measured surface temperatures. The two data sets are superimposed and the solution for heat transfer characteristics and geometry is selected that provided the best fit for both temperature data sets. The use of two sets of temperature data allows for a more accurate determination of the wall thicknesses.

BEST MODES FOR CARRYING OUT THE INVENTION

Figure 1:
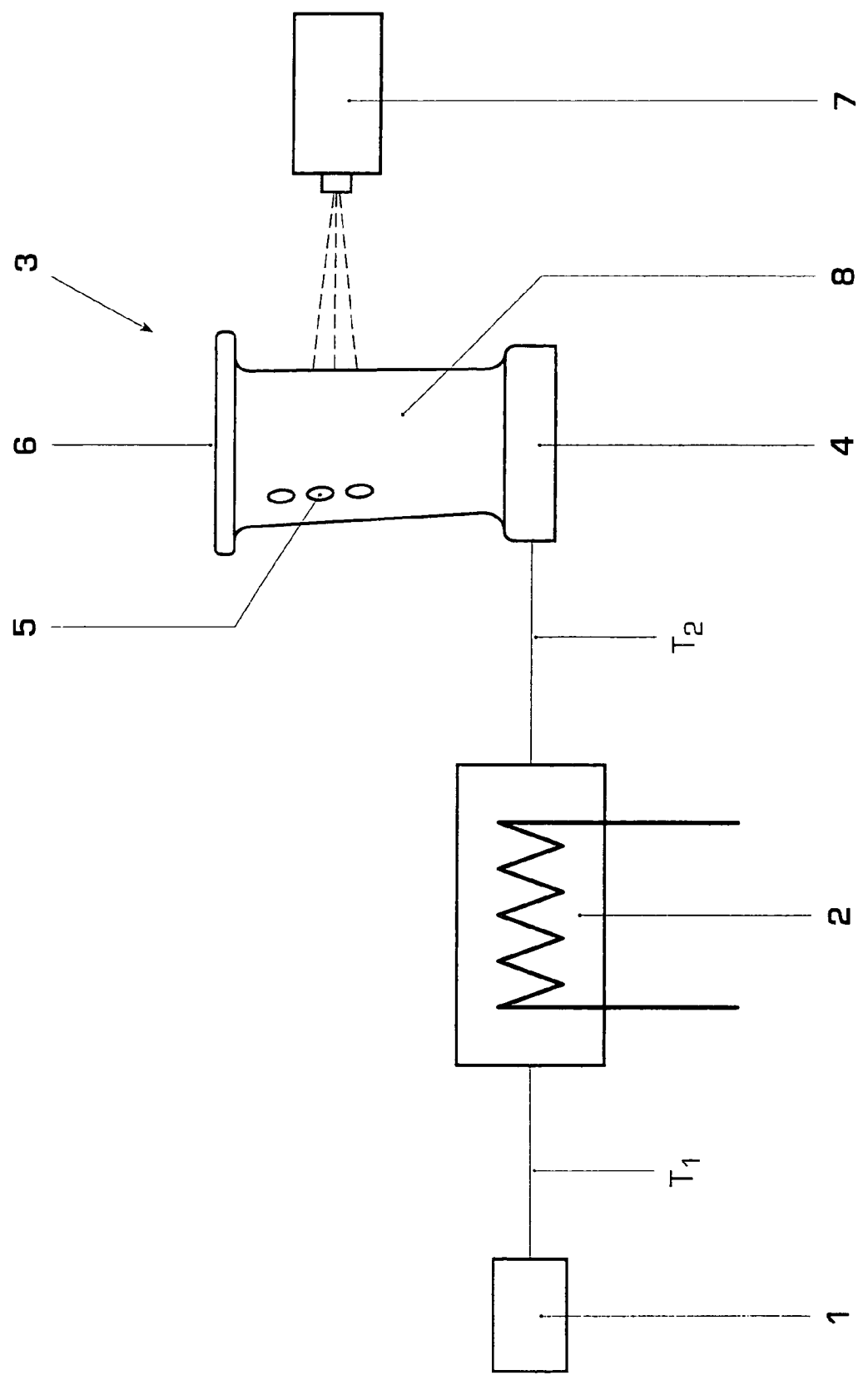
FIG. 1 shows schematically a measurement set-up for inspection of the internal structure and heat transfer characteristics of a turbine blade having a cooling structure.

FIG. 1 shows schematically a measurement set-up including a source 1 for a flow medium, most suitably air having a first temperature $T_1$. (depending on the type of body and circumstances of measurement other suitable flow media such as water, nitrogen, steam may also be used). The source 1 is connected by means of a line to an inlet to a heater 2. An outlet line leads from the heater to the inlet of the internal structure of a turbine blade 3 to be inspected. Air passing through the heater 2 is heated such that it has a selected and controlled temperature $T_2$ at a point prior to entering the cooling structure of the blade 3. The air is led to the internal cooling structure of a blade 3 via channels in the root 4 of the blade. It exits from the structure through exit holes such as film cooling holes 5 or holes in the tip region 6 of the blade. An infrared camera 7 having a pixelised detecting area is focussed onto an external surface 8 of the blade 3 and detects a thermal image of the surface 8.

Instead of heated air passed through a blade at ambient temperature, cool air may be applied in similar manner to a blade held at a raised temperature.

In lieu of an infrared camera, a pyrometer may be used as a thermal image detection device. A pyrometer allows the use of the set-up for the measurement of gas turbine components directly within a turbine engine during operation, or within a combustion system during cool down. Such a measurement set-up allows the detection of thermal surface images of the engine component throughout a temperature transient due to heating or cooling.

Figure 2:
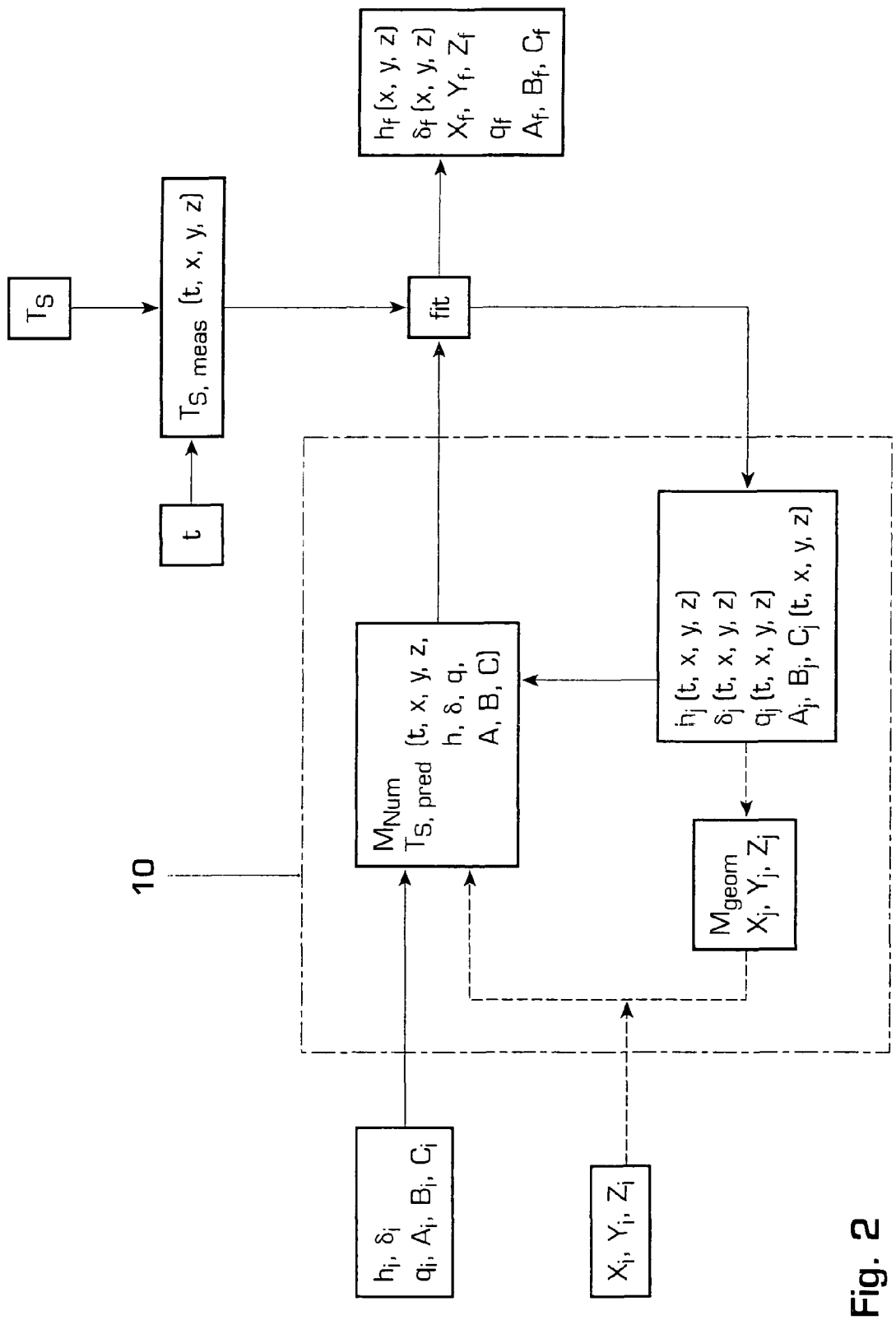
FIG. 2 shows a flow chart of the method for determining the heat transfer characteristics and geometry of a body according to the invention.

The method according to the invention a shown in FIG. 2 begins with the registration of temperatures of the blade's external surface 8, denoted by $(T_S)$, using an infrared camera or other suitable thermal imaging device. The surface temperature data are registered during the time period that the transient flow of the hot air is led through the blade's internal cooling structure and/or during a time period after the transient flow has been stopped. Thus, a thermal image history of the blade structure is established. Timing data, denoted by (t), according to which the air flow is led through the blade, is synchronised with the surface temperature data $(T_S)$ in order to obtain a temperature data set $(T_{S,\,meas}(t,x,y,z))$ as a function of time and spatial position on the blade's surface.

The surface temperatures are measured with a spatial and time resolution depending on the estimated complexity of the body's internal structure. In the case of a turbine blade for example, the time resolution may be $1/100$ second or lower. This time resolution is necessary in order to take into account the short time in which the heat passes through a wall of the blade. A suitable spatial resolution is provided by the use of infrared camera 350×250 pixels.

In a variant of the method, the spatial and time resolution of the thermal image may be changed, e.g. a smaller section of the external surface is analysed with a higher temporal resolution.

In a first version of the method, a set of initial values for heat transfer coefficients $h_i(t,x,y,z)$ and wall thicknesses $\delta_i$ (t,x,y,z) is generated as a function of time and space. The initial values are an approximation of the heat transfer characteristics established based on the external geometry and any other knowledge about the blade that may give an indication about the heat transfer characteristics.

The initial values are used, together with data on the local heat flux $q_i$ due to the flow medium heated to a known temperature $T_2$, in a numerical model $M_{num}$ that calculates for all time frames, for which actual surface temperature data has been taken, surface temperatures $T_{S,\,pred}(t,x,y,z,h,q,\delta)$ that would result on the external surface of the blade.

Further parameters $A_i, B_i, C_i$ may be included in the set of initial values to calculate the thermal response on the external surface. These other parameters may be for example material parameters such as thermal conductivity and heat capacity.

The calculated, predicted surface temperatures $T_{S,pred}(t,x,y,z,h,q,\delta)$ are compared to the temperature data $T_{S,\,meas}(t,x,y,z)$ according to a best-fit method denoted by "fit". The fit between the two sets of data may be determined according to one or more of the following criteria:
a) comparison of the absolute temperatures,
b) comparison of the change of surface temperature from the initial temperature as a function of time,
c) comparison of the local derivatives of temperature over two or more pixels with respect to time
d) comparison of the local derivatives of temperature over two or more pixels with respect to space, and
e) comparison of the combined local derivatives.

Next, a decision is made upon whether the fit between measured and modelled surface temperatures is sufficiently accurate to yield a reliable result for the heat transfer characteristics and wall thicknesses of the internal structure. If it is considered a "good" fit for the application involved, then final heat transfer coefficients $h_f(x,y,z)$, wall thicknesses $\delta_f(x,y,z)$, and other final parameters are obtained.

If the fit is considered insufficient, the difference between the measured surface temperatures and the predicted surface temperatures is used to begin an iteration 10 of the method, in which the parameters contributing to the resultant external surface temperature are optimised in order to minimise the difference between predicted and measured surface temperatures. For this, any one of the above mentioned criteria may be used, for example the difference between the local derivative with respect to space according to the measured values and the local derivative according to the model.

For the optimisation of the heat transfer coefficient and the wall thicknesses 6, any one or several of the following criteria may be chosen:
a) the walls forming flow passages within the internal structure are assumed to have a finite thickness, however to be thermodynamically thin such that the temperature gradient is assumed to be zero,
b) the said walls are assumed to have a thickness such that the temperature gradient across the wall is non-zero. In a first option, the temperature gradient is assumed to be normal to the wall. This corresponds to a one-dimensional solution; in a second option, the temperature gradient is assumed to be normal as well as not normal to the wall, which corresponds to a 2- or 3-dimensional solution. This option takes into account in particular the effects due to structures with a small radius of curvature, which is particularly the case in blade cooling structures.
c) a finite element or finite boundary model of the investigated internal structure is used to remove one unknown variable.

As a result of the optimisation, a new set of values for heat transfer coefficients hj and wall thicknesses $\delta_j$ is obtained.

Again, any of the parameters such as the local heat flux q and parameters A,B,C, e.g. material properties, may also be optimised in order to obtain new values $A_j, B_j, C_j, q_j$, for these parameters. An optimisation of the local heat flux of the transient flow medium allows to take account of the effects due to the changing temperature of the flow medium as a result of heat loss to the blade walls. This is particularly important in structures with long channels as for example in serpentine cooling structures.

The optimised values are used to calculate a new set of predicted surface temperatures which are then in turn compared to the measured temperatures. The iteration is repeated until an optimal fit is reached between predicted and measured temperatures and final values for the combination of heat transfer coefficients $h_f(x,y,z)$ and wall thicknesses $\delta_f(x,y,z)$ are determined.

In a second version of the method, denoted by broken lines in the schematic of FIG. 2, a geometry model $M_{geom}$, containing data $X_i, Y_i, Z_i$, which describe the blade, is included in the numerical model $M_{num}$. As needed, the body's geometry may be described in two or three dimensions. In the iteration process, in addition to the optimisation of the heat transfer coefficients and wall thicknesses, the spatial parameters $X_i, Y_i, Z_i$ are also optimised in order to achieve a better fit between the surface temperatures as well as to obtain the internal structure's geometry. A geometry model is particularly necessary in the case that the walls are assumed to be thermodynamically thick and have a finite thickness. A geometry is generally not necessary in the case that the walls are assumed to be thermodynamically thin.

In a variant of the method according to the invention, the geometry model of the blade is modified in terms of its layer structure, which takes into account the effects of multiple layers throughout the internal structure.

TERMS USED IN FIGURES 1 fluid medium source
2 heater for fluid medium
3 blade
4 blade root
5 exit holes, film cooling holes
6 blade tip
7 thermal image detector
8 external surface of blade
$T_1$ fluid temperature prior to heater
$T_2$ fluid temperature prior to entry into internal structure of blade
$T_S$ surface temperature data as registered by thermal image detector
$T_S(t,x,y,z)$ surface temperature data synchronised to timing data of fluid
fit comparison of measured and predicted values and determination of fit
$h_i$ initial heat transfer coefficients
$h_f(x,y,z)$ final heat transfer coefficients
$\delta_i$ initial heat wall thicknesses
$\delta_f(x,y,z)$ final heat wall thicknesses
$h_j$ optimised heat transfer coefficients
$\delta_j$ optimised heat wall thicknesses
$q_i$ initial local heat flux
$q_j$ optimised local heat flux
$A_i, B_i, C_i$ initial material parameters
$A_j, B_j, C_j$ optimised material parameters
$A_f, B_f, C_f$ final material parameters
$M_{num}$ numerical model
$M_{geom}$ geometry model for internal structure of body
$X_i, Y_i, Z_i$ initial values for geometry of body
$X_j, Y_j, Z_j$ optimised values for geometry of body
$X_f, Y_f, Z_f$ final values for geometry of body

The invention claimed is:

1. Method for determining the heat transfer characteristics and the wall thicknesses of a heat conducting body having an internal structure for a flow medium to flow through, comprising:
passing through the internal structure of the body a first flow medium having a first temperature;
registering a first thermal image of an external surface of the body as a function of time using a pixelised image detector; and
using a processor to:
process the first thermal image in order to obtain first measured surface temperatures ($T_{S,\,meas}$ (t,x,z,y)) for a given set of points in time (t) and a given set of points (x,y,z) on the surface;
predict first surface temperatures ($T_{S,\,pred}$ (t,x,y,z)) resulting from the transient flow through the body of the same external surface of the body and for the same set of points in time using a numerical model ($M_{num}$);
apply a best fit method (fit) to the first measured surface temperatures ($T_{S,\,meas}$ (t,x,z,y)) and the first predicted surface temperatures ($T_{S,\,pred}$ (t,x,y,z)) and determining a measure of fit between them; and
optimise the first predicted surface temperatures ($T_{S,\,pred}$ (t,x,y,z)) by means of an iteration until the measure of fit between the first measured surface temperatures ($T_{S,\,meas}$ (t,x,z,y)) and the first predicted surface temperatures ($T_{S,\,pred}$ (t,x,y,z)) is optimised;
wherein the numerical model ($M_{num}$) includes initial values for the heat transfer coefficients ($h_i$) and wall thicknesses ($\delta_i$) of the internal structure of the body and an estimated two- or three-dimensional geometry model ($M_{geom}$) of the internal structure of the body wherein the heat transfer coefficients, the wall thicknesses and the two- or three-dimensional geometry model ($M_{geom}$) are optimised in the iteration until the measure of fit between the first predicted temperature values ($T_{S,\,pred}$) and the first measured temperature values ($T_{S,meas}$ (t,x,z,y)) is optimised, and final heat transfer coefficients ($h_f(x,y,z)$) and wall thicknesses ($\delta_f(x,y,z)$) and final values for the geometry of the internal structure are determined that correspond to the optimised measure of fit; and
the fit between the first measured surface temperatures ($T_{S,meas}$(t,x,z,y)) and the first predicted surface temperature ($T_{S,\,pred}$(t,x,z,y)) is determined according to one or more of the following criteria;
the absolute surface temperature at a given pixel;
the change of temperature from the initial temperature over time;
the local derivative of temperature with respect to time or space;
the combined local derivative with respect to time and space.

2. Method according to claim 1 wherein the numerical model ($M_{num}$) includes an initial local heat flux ($q_i$) of the transient flow medium, which is optimised at each iteration of the method.

3. Method according to claim 1 wherein the numerical model ($M_{num}$) includes initial values for material parameters ($A_i,B_i,C_i$), which are optimised at each iteration of the method, and final material parameters ($A_f, B_f, C_f$) are obtained.

4. Method according to one of the claim 1 wherein the values included in the numerical model ($M_{num}$) are optimised according to one or more of the following criteria: the wall thicknesses are finite and the walls have a zero temperature gradient across it, the wall thicknesses are finite and the walls have a finite temperature gradient across them normal to the wall, the wall thicknesses are finite and the walls have a finite temperature gradient in two or three dimensions.

5. Method according to claim 1 comprising:
passing a second flow medium having a second temperature different from the first temperature of the first flow medium through the internal structure of the body;
registering a second thermal image of an external surface of the body as a function of time using a pixelised image detector; and
using the processor to:
process the second thermal image in order to obtain second measured surface temperatures ($T_{S,\,meas}$ (t,x,z,y)) for a given set of points in time (t) and a given set of points (x,y,z) on the surface;
predict second surface temperatures ($T_{S,\,pred}$ (t,x,y,z)) resulting from the transient flow through the body of the same external surface of the body and for the same set of points in time using a numerical model ($M_{num}$);
apply a best fit method (fit) to the second measured surface temperatures ($T_{S,\,mess}$ (t,x,z,y)) and the second predicted surface temperatures ($T_{S,\,pred}$ (t,x,y,z)) and determining a measure of fit between them; and
optimise the second predicted surface temperatures ($T_{S,\,pred}$(t,x,y,z)) by means of an iteration until the measure of fit between the second measured surface temperatures ($T_{S,\,meas}(t,x,z,y)$) and the second predicted surface temperatures ($T_{S,\,pred}(t,x,y,z)$) is optimised;

wherein the numerical model ($M_{num}$) includes initial values for the heat transfer coefficients ($h_i$) and wall thicknesses ($\delta_i$) of the internal structure of the body, which are optimised in the iteration until the measure of fit between the second predicted temperature values ($T_{S,\,pred}$) and the second measured temperature values ($T_{S,meas}(t,x,z,y)$) is optimised, and by a superposition of the first and second temperature data sets final heat transfer coefficients ($h_f(x,y,z)$) and wall thicknesses ($\delta_f(x,y,z)$) are determined that correspond to the optimised measure of fit for the first as well as the second set of temperature data.

6. Method according to claim 1 wherein the temperature of the first and/or second flow medium passing through the body is controlled by means of a heater.

7. Method according to claim 1 wherein the surface temperatures ($T_S$) registered by the image detector are synchronised with timing data (t) according to the flow medium source.

8. Method according to claim 1 wherein the pixelised thermal image detector is an infrared detector or a pyrometer.

* * * * *